US009550848B2

(12) United States Patent
Lee et al.

(10) Patent No.: US 9,550,848 B2
(45) Date of Patent: Jan. 24, 2017

(54) METHOD OF PREPARING OLEFIN-BASED POLYMER AND OLEFIN-BASED POLYMER PREPARED THEREBY

(71) Applicant: LG CHEM, LTD., Seoul (KR)

(72) Inventors: Young Woo Lee, Daejeon (KR); Hae Woong Park, Daejeon (KR); Sang Eun Park, Daejeon (KR); Choong Hoon Lee, Daejeon (KR); Don Ho Kum, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/779,788

(22) PCT Filed: Sep. 25, 2014

(86) PCT No.: PCT/KR2014/008986
§ 371 (c)(1),
(2) Date: Sep. 24, 2015

(87) PCT Pub. No.: WO2015/046931
PCT Pub. Date: Apr. 2, 2015

(65) Prior Publication Data
US 2016/0046735 A1 Feb. 18, 2016

(30) Foreign Application Priority Data
Sep. 26, 2013 (KR) .................. 10-2013-0114253

(51) Int. Cl.
C08F 4/6592 (2006.01)
C08F 4/642 (2006.01)
C08F 4/643 (2006.01)
C08F 4/653 (2006.01)
C08F 10/00 (2006.01)
C08F 210/16 (2006.01)
C08L 23/08 (2006.01)
C08F 4/659 (2006.01)
C07F 7/28 (2006.01)
B01J 31/14 (2006.01)
B01J 31/22 (2006.01)
C08F 4/52 (2006.01)
C08F 4/76 (2006.01)
C07F 17/00 (2006.01)

(52) U.S. Cl.
CPC ............ C08F 210/16 (2013.01); B01J 31/143 (2013.01); B01J 31/2295 (2013.01); C07F 7/28 (2013.01); C07F 17/00 (2013.01); C08F 4/52 (2013.01); C08F 4/65904 (2013.01); C08F 4/76 (2013.01); C08L 23/0815 (2013.01); B01J 2531/46 (2013.01); B01J 2531/48 (2013.01); C08F 4/65908 (2013.01); C08F 4/65912 (2013.01); C08F 2420/02 (2013.01); C08F 2420/06 (2013.01); C08L 2205/025 (2013.01)

(58) Field of Classification Search
CPC . C08F 4/6592; C08F 4/65908; C08F 4/65912; C08F 10/00; C08F 4/65904; C08F 210/16; C08L 23/0815
See application file for complete search history.

(56) References Cited

U.S. PATENT DOCUMENTS

| 5,064,802 | A | 11/1991 | Stevens et al. |
|---|---|---|---|
| 5,539,076 | A | 7/1996 | Nowlin et al. |
| 6,214,953 | B1 | 4/2001 | Oh et al. |
| 6,548,686 | B2 | 4/2003 | Nabika et al. |
| 6,576,723 | B1 | 6/2003 | Bohnen et al. |
| 7,504,354 | B2 | 3/2009 | Elder et al. |
| 9,096,575 | B2 | 8/2015 | Lee et al. |
| 2005/0054791 | A1 | 3/2005 | Nowlin et al. |
| 2007/0225158 | A1 | 9/2007 | Lee et al. |
| 2008/0021183 | A1 | 1/2008 | Graham et al. |
| 2010/0062927 | A1 | 3/2010 | Lee et al. |
| 2010/0087609 | A1 | 4/2010 | Park et al. |
| 2010/0093959 | A1 | 4/2010 | Hong et al. |
| 2010/0121006 | A1 | 5/2010 | Cho et al. |
| 2011/0086990 | A1 | 4/2011 | Graham et al. |
| 2011/0152529 | A1 | 6/2011 | Lee et al. |
| 2011/0160413 | A1 | 6/2011 | Lee et al. |
| 2011/0172451 | A1 | 7/2011 | Lee et al. |
| 2011/0177935 | A1 | 7/2011 | Lee et al. |

(Continued)

FOREIGN PATENT DOCUMENTS

| CN | 1227570 A | 9/1999 |
|---|---|---|
| CN | 101213218 A | 7/2008 |

(Continued)

OTHER PUBLICATIONS

Chinese Office Action and Search Report dated Feb. 23, 2016, for Chinese Application No. 201480001887.4 with the English translation of the Office Action.

(Continued)

Primary Examiner — Caixia Lu
(74) Attorney, Agent, or Firm — Birch, Stewart, Kolasch & Birch, LLP

(57) ABSTRACT

The present invention relates to a method of preparing an olefin-based polymer including a step of polymerizing an olefin monomer in the presence of a catalyst composition including a cis isomer and a trans isomer. According to the method of preparing an olefin-based polymer according to an embodiment of the present invention, similar level of density and molecular weight may be exhibited with a relatively smaller amount of octene when compared to that of a common polymer. Thus, a stable olefin-based polymer having good copolymerization properties may be prepared.

14 Claims, No Drawings

(56) References Cited

U.S. PATENT DOCUMENTS

| | | | |
|---|---|---|---|
| 2013/0203949 A1 | 8/2013 | Lee et al. |
| 2013/0211020 A1 | 8/2013 | Lee et al. |
| 2013/0211021 A1 | 8/2013 | Lee et al. |
| 2013/0211023 A1 | 8/2013 | Lee |
| 2013/0211024 A1 | 8/2013 | Lee et al. |
| 2013/0296497 A1 | 11/2013 | Jeong et al. |
| 2015/0011770 A1 | 1/2015 | Lee et al. |

FOREIGN PATENT DOCUMENTS

| | | |
|---|---|---|
| CN | 101296932 A | 10/2008 |
| CN | 102834402 A | 12/2012 |
| EP | 2 873 671 A1 | 5/2015 |
| JP | 2002-516358 A | 6/2002 |
| JP | 2003-201308 A | 7/2003 |
| JP | 2010-514836 A | 5/2010 |
| JP | 2010-526203 A | 7/2010 |
| JP | 2013-527271 A | 6/2013 |
| KR | 10-2001-0020425 A | 3/2001 |
| KR | 10-2005-0035183 A | 4/2005 |
| KR | 10-2007-0096465 A | 10/2007 |
| KR | 10-0820542 B1 | 4/2008 |
| KR | 10-2008-0049981 A | 6/2008 |
| KR | 10-2008-0065868 A | 7/2008 |
| KR | 10-2008-0097019 A | 11/2008 |
| KR | 10-2008-0101542 A | 11/2008 |
| KR | 10-0964093 B1 | 6/2010 |
| KR | 10-2010-0083076 A | 7/2010 |
| KR | 10-0986301 B1 | 10/2010 |
| KR | 10-2012-0024427 A | 3/2012 |
| KR | 10-1175338 B1 | 8/2012 |
| KR | 10-1299375 B1 | 8/2013 |
| WO | WO 2015/046930 A1 | 4/2015 |
| WO | WO 2015/046931 A1 | 4/2015 |
| WO | WO 2015/046932 A1 | 4/2015 |

OTHER PUBLICATIONS

Chen et al., "A Novel Phenolate "Constrained Geometry" Catalyst System. Efficient Synthesis, Structural Characterization, and α-Olefin Polymerization Catalysis", Organometallics, 1997, vol. 16, pp. 5958-5963.

Christie et al., "Novel Routes to Bidentate Cyclopentadienyl-Alkoxide Complexes of Titanium: Synthesis of ($\eta^5$-σ-$C_5R^1_4CHR^2CH_2CR^3R^4O)TiCl_2$", Organometallics, 1999, vol. 18, pp. 348-359.

Gibson et al., "Advances in Non-Metallocene Olefin Polymerization Catalysis", Chemical Reviews, 2003, vol. 103, pp. 283-315.

Gielens et al., "Titanium Hydrocarbyl Complexes with a Linked Cyclopentadienyl-Alkoxide Ancillary Ligand; Participation of the Ligand in an Unusual Activation of a (Trimethylsilyl)methyl Group", Organometallics, 1998, vol. 17, pp. 1652-1654.

International Search Report, issued in PCT/KR2014/008986, dated Dec. 23, 2014.

Kim et al., "Preparation of Thiophene-Fused and Tetrahydroquinoline-Linked Cyclopentadienyl Titanium Complexes for Ethylene/α-Olefin Copolymerization", Catalysts, 2013, vol. 3, pp. 104-124.

McDonagh et al., "Organometallic complexes for nonlinear optics Part 21. Syntheses and quadratic hyperpolarizabilities of alkynyl complexes containing optically active 1,2bis(methylphenylphosphino)benzene ligands", Journal of Organometallic Chemistry, 2000, vol. 610, pp. 71-79.

Turner et al., "Facile resolution of constrained geometry indenyl-phenoxide ligation", Chemical Communications, 2003, pp. 1034-1035.

Zhang et al., "Constrained Geometry Tetramethylcyclopentadiehyl-phenoxytitanium Dichlorides: Template Synthesis, Structures, and Catalytic Properties for Ethylene Polymerization", Organometallics, 2004, vol. 23, pp. 540-546.

Extended European Search Report for European Application No. 14812388.8, dated Sep. 1, 2015.

International Search Report, dated Dec. 26, 2014, for International Application No. PCT/KR2014/008985.

Nayab et al., "Synthesis and characterization of novel tungsten complexes and their activity in the ROMP of cyclic olefins," Polyhedron, vol. 42, 2012 (Available online May 18, 2012), pp. 102-109.

Rau et al., "Synthesis and application in high-pressure polymerization of a titanium complex with a linked cyclopentadienyl-phenoxide ligand," Journal of Organometallic Chemistry, 2000, vol. 608, pp. 71-75.

METHOD OF PREPARING OLEFIN-BASED POLYMER AND OLEFIN-BASED POLYMER PREPARED THEREBY

TECHNICAL FIELD

The present invention relates to a method of preparing an olefin-based polymer and an olefin-based polymer prepared thereby.

BACKGROUND ART

[Me$_2$Si(Me$_4$C$_5$)NtBu] TiCl$_2$ (Constrained-Geometry Catalyst, hereinafter, will be abbreviated as CGC) was reported by Dow Co. in the early 1990s (U.S. Pat. No. 5,064,802), and excellent aspects of the CGC in the copolymerization reaction of ethylene and alpha-olefin may be summarized in the following two points when compared to commonly known metallocene catalysts.

(1) At a high polymerization temperature, high activity is shown and a polymer having high molecular weight is produced, and (2) the copolymerization degree of alpha-olefin having large steric hindrance such as 1-hexene and 1-octene is excellent.

Meanwhile, a copolymer prepared by using the CGC catalyst includes a small amount of a low molecular weight part and may have improved physical properties such as strength, etc. when compared to a copolymer prepared by using a common Zeigler-Natta catalyst.

However, despite the above-described merits, the copolymer prepared by using the CGC catalyst has the defects of deteriorating processability when compared to the polymer prepared by using the common Zeigler-Natta catalyst.

U.S. Pat. No. 5,539,076 discloses a metallocene/non-metallocene blend catalyst system for preparing a specific bimodal copolymer having high density. The catalyst system is supported on an inorganic support. A supported Zeigler-Natta catalyst and a metallocene catalyst system has a drawback that a supported hybrid catalyst has lower activity than a homogeneous single catalyst, and the preparation of an olefin-based polymer having appropriate properties according to use is difficult. In addition, since the olefin-based polymer is prepared in a single reactor, gel that may be generated during the performing of a blending method may be produced, the insertion of a comonomer in a high molecular weight part may be difficult, the shape of a produced polymer may be poor, two polymer components may not be mixed homogeneously, and the control of quality may be difficult.

Thus, the development of an olefin-based polymer that may overcome the drawbacks of a common olefin-based polymer and provide improved physical properties is still required.

PRIOR ART DOCUMENTS

Patent Documents

U.S. Pat. No. 5,064,802
U.S. Pat. No. 6,548,686

Non-Patent Documents

Chem. Rev. 2003, 103, 283
Organometallics 1997, 16, 5958
Organometallics 2004, 23, 540
Chem. Commun. 2003, 1034
Organometallics 1999, 18, 348
Organometallics 1998, 17, 1652
J. Organomet. Chem. 2000, 608, 71

DISCLOSURE OF THE INVENTION

Technical Problem

The present application provides a method of preparing an olefin-based polymer and an olefin-based polymer prepared thereby.

Technical Solution

According to an embodiment of the present application, a method of preparing an olefin-based polymer including a step of polymerizing an olefin monomer in the presence of a catalyst composition including a cis isomer and a trans isomer of a transition metal compound is provided.

According to an embodiment of the present application, an olefin-based polymer prepared by the above-described method of preparing an olefin-based polymer, is provided.

Advantageous Effects

According to the method of preparing an olefin-based polymer according to an embodiment of the present invention, a polymer having density and molecular weight of similar level as those of a common polymer may be obtained even using a relatively smaller amount of octene than that used for preparing the common polymer, thereby improving copolymerization properties further.

In addition, the olefin-based polymer prepared by the above preparation method has narrow molecular weight distribution and constant monomer content according to the molecular weight even in the presence of a single catalyst composition. In addition, an olefin-based polymer including two elution temperature 1 (Te1) and elution temperature 2 (Te2) may be prepared when measuring temperature rising elution fractionation (TREF), and an olefin-based polymer having better properties of controlling fractional ratios of TREF peaks and so being more stable, may be prepared.

BEST MODE FOR CARRYING OUT THE INVENTION

According to an embodiment of the present application, a method of preparing an olefin-based polymer including a step of polymerizing an olefin monomer in the presence of a catalyst composition including a cis isomer and a trans isomer of a transition metal compound is provided.

In the present application, the term "a polymer" denotes a polymer compound prepared by the polymerization of monomers having the same or different types. The general term "the polymer" includes "a hybrid polymer" as well as "a homopolymer," "a copolymer" and "a tercopolymer."

"The hybrid polymer" denotes a polymer prepared by the polymerization of at least two different types of monomers. The general term "the hybrid polymer" denotes "the copolymer" (commonly used for denoting a polymer prepared using two different types of monomers) and "the tercopolymer" (commonly used for denoting a polymer prepared using three different types of monomers). "The hybrid polymer" includes a polymer prepared by the polymerization of at least four different types of monomers.

In the present application, the term "semi-crystalline" designates a polymer having a first transition temperature measured by TREF, differential scanning calorimetry (DSC), or other equivalent technique, a crystalline melting point (Tm), an elution point, etc. The density, the Tm, the elution point, etc. of the quasicrystal may be dependent on the crystallinity thereof. The term "amorphous" designates a polymer having no crystalline melting point when measured by TREF, DSC, or other equivalent technique.

According to the method of preparing an olefin-based polymer according to an embodiment of the present invention, a polymer having density and molecular weight of similar level as those of a common polymer may be obtained even using a relatively smaller amount of octene than that used for preparing the common polymer, thereby improving copolymerization properties further.

The olefin-based polymer according to the present invention has a narrow molecular weight distribution, includes two of Te1 and Te2 when measuring TREF. In addition, the control of the fractional ratios of TREF peaks is better, and a more stable olefin-based polymer may be prepared.

The olefin-based polymer satisfying the above physical properties shows excellent impact strength and processability and may be used in diverse fields and uses including wrapping, construction, daily supplies, etc. such as a material of an automobile, a wire, a toy, a fiber, a medicine, etc.

In the method of preparing an olefin-based polymer according to another embodiment of the present application, the cis isomer (c) and the trans isomer (t) of the transition metal compound is selected in an amount range by weight (c:t) of 1-99:99-1.

According to another embodiment of the present application, the cis isomer and the trans isomer of the transition metal compound is included, and the weight ratio of the cis isomer (c) and the trans isomer (t) of the transition metal compound is selected in a range of 1-49:99-51, or 51-99:49-1.

According to further another embodiment of the present application, the cis isomer and the trans isomer of the transition metal compound is included, and the weight ratio of the cis isomer (c) and the trans isomer (t) of the transition metal compound is 50:50.

In the present invention, the amounts of the cis isomer and the trans isomer of the transition metal compound may be obtained by using $^1$H-NMR.

The olefin-based polymer according to an embodiment of the present application may be prepared by polymerizing an olefin monomer using a catalyst composition including a transition metal compound of the following Formula 1.

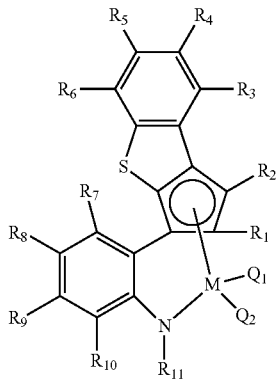

<Formula 1> in the above Formula 1,

M is a transition metal in group 4, $Q_1$ and $Q_2$ are the same or different and independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_1$ to $R_6$ are the same or different and independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14 substituted with hydrocarbyl having 1 to 20 carbon atoms; $R_1$ and $R_2$ may be connected from each other, or at least two of $R_3$ to $R_6$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms or aryl having 6 to 20 carbon atoms, and $R_7$ to $R_{11}$ are the same or different and independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; at least two adjacent to each other of $R_7$ to $R_{11}$ may be connected to each other to form an aliphatic ring having 5 to 20 carbon atoms or an aromatic ring having 6 to 20 carbon atoms; the aliphatic ring or the aromatic ring may be substituted with halogen, alkyl having 1 to 20 carbon atoms, alkenyl having 2 to 20 carbon atoms or aryl having 6 to 20 carbon atoms.

$R_1$ to $R_{11}$ may be independently unsubstituted or substituted, and for the substituted $R_1$ to $R_{11}$, a substituent may be halogen, alkyl having 1 to 20 carbon atoms, hydrocarbyl having 1 to 20 carbon atoms, alkoxy having 1 to carbon atoms or aryloxy having 6 to 20 carbon atoms.

In the transition metal compound of the above Formula 1 described in the present application, a metal site is connected to a cyclopentadienyl ligand connected to a phenylene bridge introducing an amido group, and the structure thereof has a narrow Cp-M-N angle and a wide $Q_1$-M-$Q_2$ angle to which a monomer may approach. In addition, different from a CGC structure connected by a silicon bridge, the sites of cyclopentadiene fused with benzothiophene via the bonding of a ring shape, the phenylene bridge, nitrogen and the metal are connected in order to form a stable and rigid pentagonal ring structure in the compound structure represented by the above Formula 1.

Thus, when applying these compounds for the polymerization of olefin after reacting with a cocatalyst such as methyl aluminoxane or $B(C_6F_5)_3$ and activating, polyolefin having high activity, high molecular weight and high copolymerization degree may be produced even at a high polymerization temperature. Particularly, since a large amount of alpha-olefin may be introduced as well as linear polyethylene having low density of 0.910-0.930 g/cc due to the structural characteristics of the catalyst, a polyolefin copolymer having extremely low density of less than 0.910 g/cc may be produced.

In particular, a polymer having narrow molecular weight distribution (MWD), good copolymerization degree and high molecular weight in a low density region may be prepared by using a catalyst composition including the transition metal compound.

In addition, diverse substituents may be introduced in a cyclopentadienyl group fused with benzothiophene and quinolines, and electronic and steric environment around a metal may be easily controlled, and so, the structure and physical properties of the polyolefin thus produced may be controlled. The compound of the above Formula 1 may be preferably used for preparing a catalyst for polymerizing an olefin monomer, however the present invention is not limited thereto. The transition metal compound may be used in any other applicable fields.

According to another embodiment of the present application, $R_7$ to $R_{10}$ are hydrogen.

According to another embodiment of the present application, $R_{11}$ may be unsubstituted or substituted alkyl having 1 to 20 carbon atoms, aryl having 6 to 20 carbon atoms or alkylaryl having 7 to 20 carbon atoms.

In this case, a substituent may be halogen, alkyl having 1 to 20 carbon atoms, hydrocarbyl having 1 to 20 carbon atoms, alkoxy having 1 to 20 carbon atoms or aryloxy having 6 to 20 carbon atoms.

In this case, the transition metal compound may be one or at least two transition metal compounds selected from the group consisting of the compounds represented by the following Formulae.

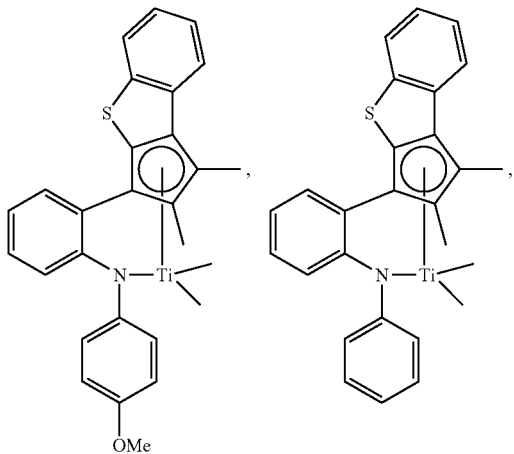

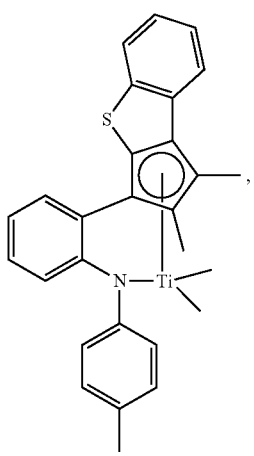

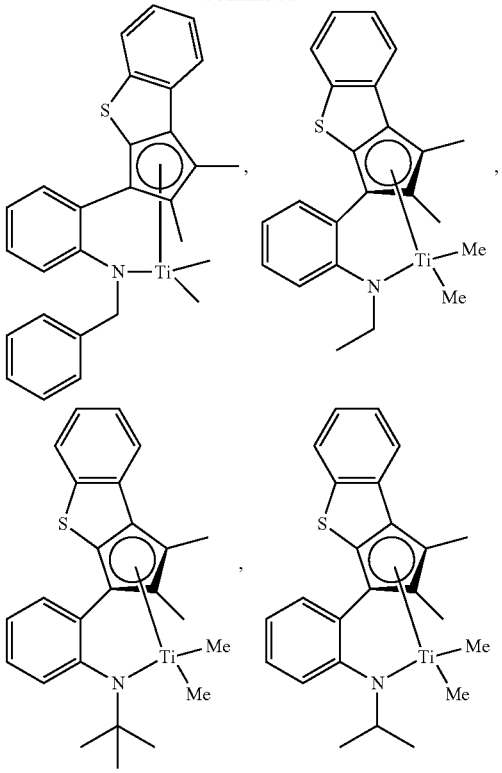

According to another embodiment of the present application, $R_{11}$ is connected to adjacent $R_{10}$ from each other to form an aliphatic ring having 5 to 20 carbon atoms or an aromatic ring having 6 to 20 carbon atoms. In addition, the aliphatic ring or the aromatic ring may be substituted with halogen, alkyl having 1 to 20 carbon atoms, alkenyl having 2 to 20 carbon atoms or aryl having 6 to 20 carbon atoms.

In this case, the transition metal compound may be represented, for example, by the following Formula 2.

<Formula 2>

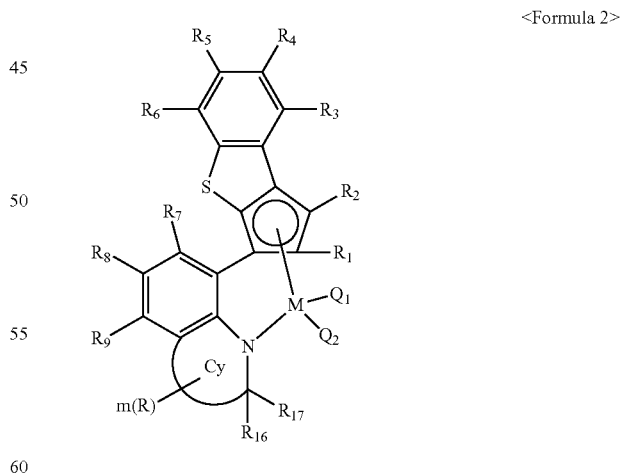

in the above Formula 2,

M, $Q_1$, $Q_2$, and $R_1$ to $R_9$ are the same as defined in the above Formula 1, Cy is a five-membered or six-membered aliphatic ring, and R, $R_{16}$ and $R_{17}$ are independently hydrogen; alkyl having 1 to 20 carbon atoms; alkenyl having 2 to 20 carbon atoms;

aryl having 6 to 20 carbon atoms; alkylaryl having 7 to 20 carbon atoms; or arylalkyl having 7 to 20 carbon atoms;

when Cy is the five-membered aliphatic ring, m is an integer from 0 to 2, and when Cy is the six-membered aliphatic ring, m is an integer from 0 to 4.

According to an embodiment of the present application, the transition metal compound may have stereoisomers having different steric conformation between substituents in a molecule including at least one chiral center. For example, in the compound of the above Formula 1, carbon of $R_{11}$ may be a chiral center, and a molecule including the chiral center may have a cis structure and a trans structure, having different steric conformation between substituents.

According to an embodiment of the present application, the cis isomer of the transition metal compound according to the embodiment may be represented by the following Formula 3, and the trans isomer thereof may be represented by the following Formula 4.

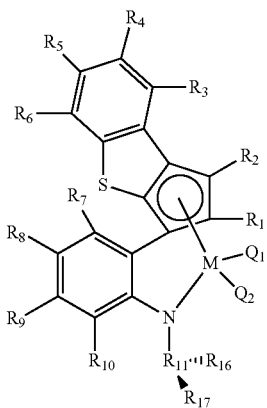

<Formula 3>

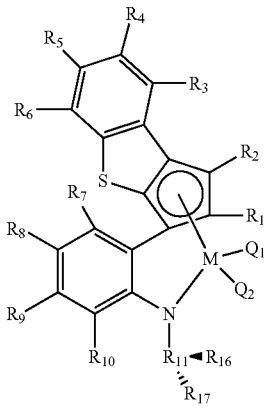

<Formula 4> in the above Formulae 3 and 4,

M, $Q_1$, $Q_2$, and $R_1$ to $R_{11}$ are the same as defined in the above Formula 1, and $R_{16}$ and $R_{17}$ are the same or different and independently hydrogen, alkyl having 1 to 20 carbon atoms; alkenyl having 2 to 20 carbon atoms; cycloalkyl having 3 to 20 carbon atoms; aryl having 6 to 20 carbon atoms; alkylaryl having 7 to 20 carbon atoms; arylalkyl having 7 to 20 carbon atoms; or heteroaryl having 2 to 20 carbon atoms.

According to another embodiment of the present application, the cis isomer (c) of the transition metal compound of the embodiment may be represented by the following Formula 5, and the trans isomer (t) thereof may be represented by the following Formula 6.

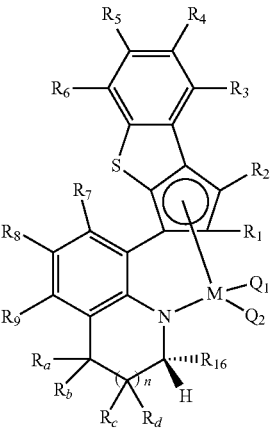

<Formula 5>

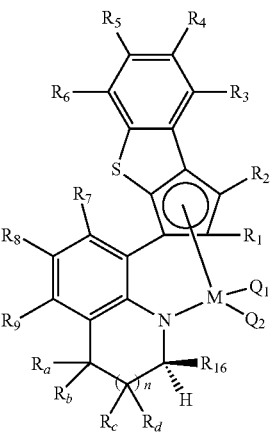

<Formula 6> in the above Formulae 5 and 6,

M, $Q_1$, $Q_2$ and $R_1$ to $R_9$ are the same as defined in the above Formula 1, n is 0 or 1, $R_a$ to $R_d$ are the same or different and independently hydrogen; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms, where at least two of adjacent $R_a$ to $R_d$ are connected to each other to form an aliphatic ring having 5 to carbon atoms or an aromatic ring having 6 to 20 carbon atoms, and the aliphatic ring or the aromatic ring may be substituted with halogen, alkyl having 1 to 20 carbon atoms, alkenyl having 2 to 20 carbon atoms, or aryl having 6 to 20 carbon atoms, and $R_{16}$ is alkyl having 1 to 20 carbon atoms; alkenyl having 2 to 20 carbon atoms; cycloalkyl having 3 to 20 carbon atoms; aryl having 6 to 20 carbon atoms; alkylaryl having 7 to 20 carbon atoms; arylalkyl having 7 to 20 carbon atoms; or heteroaryl having 2 to 20 carbon atoms.

In an embodiment of the present application, alkyl and alkenyl may be a linear or branched chain alkyl or alkenyl.

In another embodiment of the present application, silyl may be a substituted silyl with alkyl having 1 to 20 carbon atoms, for example, trimethylsilyl or triethylsilyl.

In a further another embodiment of the present application, aryl includes a single ring aryl or a polyring aryl, for example, phenyl, naphthyl, anthryl, phenanthryl, crysenyl, pyrenyl, etc.

According to a further another embodiment of the present application, $R_1$ and $R_2$ in the above Formula 1 are the same or different and are independently alkyl having 1 to 20 carbon atoms.

According to a further another embodiment of the present application, $R_1$ and $R_2$ in the above Formula 1 are the same or different and are independently alkyl having 1 to 6 carbon atoms.

According to a further another embodiment of the present application, $R_1$ and $R_2$ in the above Formula 1 are methyl.

According to a further another embodiment of the present application, $R_3$ to $R_6$ in the above Formula 1 are the same or different and independently hydrogen; alkyl having 1 to 20 carbon atoms; or alkenyl having 2 to 20 carbon atoms.

According to a further another embodiment of the present application, $R_3$ to $R_6$ in the above Formula 1 are the same or different and independently hydrogen; or alkyl having 1 to 20 carbon atoms.

According to a further another embodiment of the present application, $R_3$ to $R_6$ in the above Formula 1 are the same or different and independently hydrogen.

According to a further another embodiment of the present application, in the above Formulae 5 and 6, where n is 0, $R_7$ to $R_9$ and $R_a$ to $R_d$ are the same or different and independently hydrogen; alkyl having 1 to 20 carbon atoms; or alkenyl having 2 to 20 carbon atoms.

According to a further another embodiment of the present application, in the above Formulae 5 and 6, where n is 0, $R_7$ to $R_9$ and $R_a$ to $R_d$ are the same or different and independently hydrogen; or alkyl having 1 to 20 carbon atoms.

According to a further another embodiment of the present application, in the above Formulae 5 and 6, where n is 0, $R_7$ to $R_9$ and $R_a$ to $R_d$ are hydrogen.

According to a further another embodiment of the present application, in the above Formulae 5 and 6, where n is 1, $R_7$ to $R_9$ and $R_a$ to $R_d$ are the same or different and independently hydrogen; alkyl having 1 to 20 carbon atoms; or alkenyl having 2 to 20 carbon atoms.

According to a further another embodiment of the present application, in the above Formulae 5 and 6, where n is 1, $R_7$ to $R_9$ and $R_a$ to $R_d$ are the same or different and independently hydrogen; or alkyl having 1 to 20 carbon atoms.

According to a further another embodiment of the present application, in the above Formulae 5 and 6, where n is 1, $R_7$ to $R_9$ and $R_a$ to $R_d$ are hydrogen.

According to a further another embodiment of the present application, in the above Formulae 5 and 6, $R_{16}$ is alkyl having 1 to 20 carbon atoms.

According to a further another embodiment of the present application, in the above Formulae 5 and 6, $R_{16}$ is alkyl having 1 to 6 carbon atoms.

According to a further another embodiment of the present application, in the above Formulae 5 and 6, $R_{16}$ is methyl; or n-butyl.

According to a further another embodiment of the present application, M in the above Formula 1 is Ti, Hf or Zr.

In the present application, the catalyst composition is characterized in that a metal site is connected to a cyclopentadienyl ligand connected to a phenylene bridge introducing an amido group, and the structure thereof has a narrow Cp-M-N angle and a wide $Q_1$-M-$Q_2$ angle to which a monomer may approach.

In addition, different from a CGC structure connected by a silicon bridge, the sites of cyclopentadiene fused with benzothiophene via the bonding of a ring shape, the phenylene bridge, nitrogen and the metal are connected in order to form a stable and rigid pentagonal ring structure in the compound structure represented by the above Formula 1.

In addition, since an isomer mixture has different stereoselectivity, when applying the isomer mixture for the polymerization of an olefin after reacting with a cocatalyst such as methyl aluminoxane or $B(C_6F_5)_3$ and activating, polyolefin having high activity, high molecular weight and high copolymerization degree may be produced even at a high polymerization temperature.

Particularly, since a large amount of alpha-olefin may be introduced as well as linear polyethylene having low density of 0.910-0.930 g/cc due to the structural characteristics of the catalyst, a polyolefin copolymer having extremely low density of less than 0.910 g/cc may be produced.

In particular, a polymer having narrow MWD, good copolymerization degree and high molecular weight in a low density region may be prepared by using a catalyst composition including the isomer mixture. In addition, diverse substituents may be introduced in a cyclopentadienyl group fused with benzothiophene and quinoline, and electronic and steric environment around a metal may be easily controlled, and so, the structure and physical properties of the polyolefin thus produced may be controlled.

The catalyst composition may be preferably used for preparing a catalyst for polymerizing an olefin monomer, however the present invention is not limited thereto. The transition metal compound may be used in any other applicable fields.

According to an embodiment of the present application, the catalyst composition of the above Formula 1 may be prepared by the following steps of a) to d):

a) a step of preparing a compound represented by the following Formula 8 by performing a reaction of an amine compound represented by the following Formula 7 with an alkyl lithium and adding a compound including a protecting group (—$R_0$);

b) a step of preparing an amine compound represented by the following Formula 10 by performing a reaction of the compound represented by the following Formula 8 with an alkyl lithium and adding a ketone compound represented by the following Formula 9;

c) a step of preparing a dilithium compound represented by the following Formula 11 by performing a reaction of a compound represented by the above Formula 10 with n-butyllithium; and d) a step of preparing a catalyst composition represented by Formula 1 by performing a reaction of a compound represented by the following Formula 11 with $MCl_4$ (M=transition metal in group 4) and an organ lithium compound.

<Formula 7>

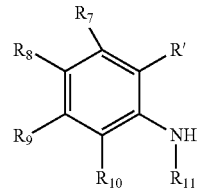

-continued

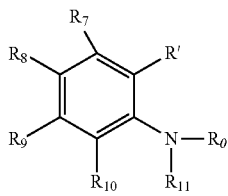
<Formula 8>

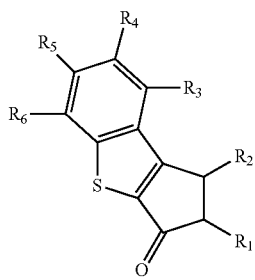
<Formula 9>

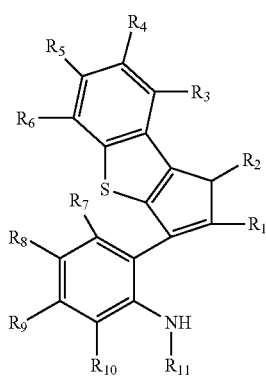
<Formula 10>

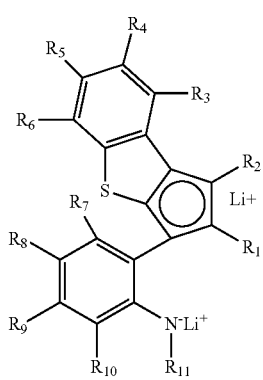
<Formula 11> in the above Formulae 7 to 11,

R' is hydrogen, $R_0$ is a protecting group, and other substituents are the same as defined in Formula 1.

In the above step a), the compound including the protecting group may be selected from trimethylsilyl chloride, benzyl chloride, t-butoxycarbonyl chloride, benzyloxycarbonyl chloride and carbon dioxide.

When the compound including the protecting group is the carbon dioxide, the above Formula 8 may be a lithium carbamate compound represented by the following Formula 8a.

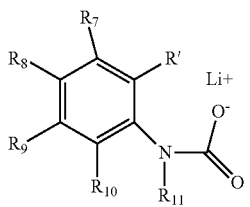
<Formula 8a>

The substituents are the same as defined in Formula 1.

According to a particular embodiment, the compound of Formula 1 may be prepared by the following Reaction 1.

<Reaction 1>

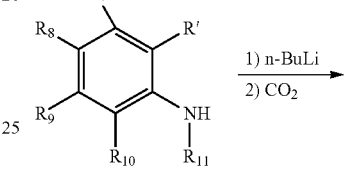

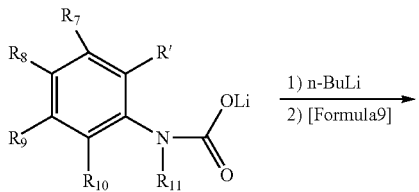

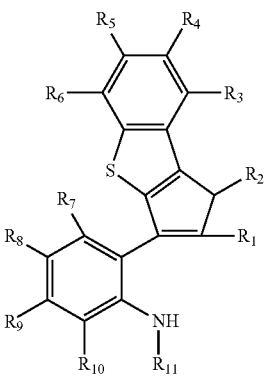

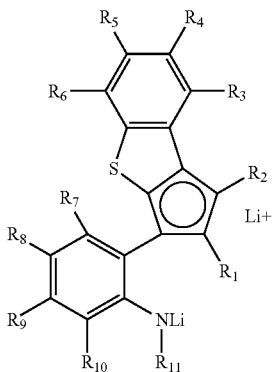

-continued

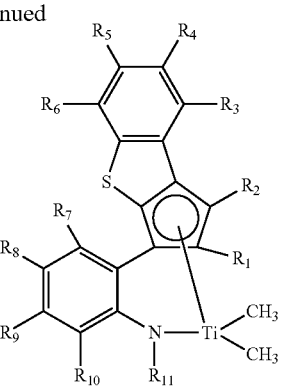

In the above Reaction 1, substituents are the same as defined above.

The present application also provides a catalyst composition including the compound of the above Formula 1.

The catalyst composition may further include a cocatalyst. Known materials in this field may be used as the cocatalyst.

For example, the catalyst composition may further include at least one of the following Formulae 12 to 14 as the cocatalyst.

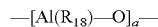 <Formula 12>

In the above Formula, each $R_{18}$ is independently a halogen radical; a hydrocarbyl radical having 1 to 20 carbon atoms; or a hydrocarbyl radical substituted with halogen and having 1 to 20 carbon atoms, and a is an integer greater than or equal to 2.

 <Formula 13>

In the above Formula, D is aluminum or boron, and $R_{18}$ is the same as in the above Formula 12.

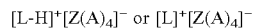 <Formula 14>

In the above Formula, L is a neutral or cationic Lewis acid, H is a hydrogen atom, Z is an element in group 13, and A is independently aryl having 6 to 20 carbon atoms or alkyl having 1 to 20 carbon atoms, where at least one hydrogen atom may be substituted with a substituent, and the substituent is halogen, hydrocarbyl having 1 to 20 carbon atoms, alkoxy having 1 to 20 carbon atoms, or aryloxy having 6 to 20 carbon atoms.

According to an embodiment of the present application, first, a method including a step of obtaining a mixture by contacting the catalyst composition with a compound represented by the above Formula 12 or Formula 13; and a step of adding a compound represented by the above Formula 14 into the mixture is provided as the method of preparing the catalyst composition.

Second, a method of preparing a catalyst composition by contacting the catalyst composition with the compound represented by the above Formula 14 is provided.

According to another embodiment of the present application, in the first method among the preparing methods of the catalyst composition according to the above embodiment, the molar ratio of the compound represented by the above Formula 12 or Formula 13 with respect to the catalyst composition may preferably be from 1:2 to 1:5,000, may more preferably be from 1:10 to 1:1,000, and may most preferably be from 1:20 to 1:500.

Meanwhile, the molar ratio of the compound represented by the above Formula 14 with respect to the catalyst composition may preferably be from 1:1 to 1:25, may more preferably be from 1:1 to 1:10, and may most preferably be from 1:1 to 1:5.

In the case that the molar ratio of the compound represented by the above Formula 12 or Formula 13 with respect to the catalyst composition is less than 1:2, the amount of an alkylating agent is very small, and the alkylation of a metal compound may not be completely carried out, and when the molar ratio exceeds 1:5,000, the activation of the alkylated metal compound may not be completely carried out due to the side reaction of the remaining excessive alkylating agent with the activation agent of the above Formula 14 even though the alkylation of the metal compound may be carried out.

In addition, in the case that the molar ratio of the compound represented by the above Formula 14 with respect to the transition metal compound of the above Formula 1 is less than 1:1, the amount of the activation agent is relatively small, and the activation of the metal compound may not be completely carried out, thereby deteriorating the activity of the catalyst composition prepared. In the case that the molar ratio exceeds 1:25, the remaining excessive amount of the activation agent may decrease the economic performance in consideration of the unit price of the catalyst composition, or the purity of a polymer thus produced may be decreased even though the activation of the metal compound may be completely carried out.

According to another embodiment of the present application, in the second method among the preparing methods of the catalyst composition according to the above embodiment, the molar ratio of the compound represented by the above Formula 14 with respect to the catalyst composition may preferably be from 1:1 to 1:500, may more preferably be from 1:1 to 1:50, and may most preferably be from 1:2 to 1:25. In the case that the molar ratio is less than 1:1, the amount of the activation agent is relatively small, and the activation of the metal compound may not be completely carried out, thereby deteriorating the activity of the catalyst composition prepared. In the case that the molar ratio exceeds 1:500, the remaining excessive amount of the activation agent may decrease the economic performance in consideration of the unit price of the catalyst composition, or the purity of a polymer thus produced may be decreased even though the activation of the metal compound may be completely carried out.

According to another embodiment of the present application, a hydrocarbon solvent such as pentane, hexane, heptane, etc., or an aromatic solvent such as benzene, toluene, etc. may be used as a reaction solvent during the preparation of the catalyst composition. However, the solvent is not limited thereto, and all solvents useful in this field may be used.

In addition, the composition may further include an additive. For example, the composition may include a compound containing a hetero atom. Particularly, the compound containing a hetero atom may include a heterocyclic compound; or an alkane containing a hetero atom.

Examples of the heterocyclic compound may include an aromatic ring containing a hetero atom; a heterocycloalkane; or a heterocycloalkene.

Examples of the alkane containing a hetero atom may include an alkane including an amine group or an ether group.

The heteroaromatic ring; the heterocycloalkane; or the heterocycloalkene may include a five membered or six membered ring.

The compound containing a hetero atom may include O, S, Se, N, P or Si as the hetero atom.

The compound containing a hetero atom may include one hetero atom.

The compound containing a hetero atom may be substituted, and in the case that the compound containing a hetero atom is substituted, the compound may be substituted with at least one selected from the group consisting of hydrogen, methyl, phenyl and benzyl.

Examples of the compound containing a hetero atom may include at least one selected from the group consisting of pyridine, 3,5-dimethylpyridine, 2,4,6-trimethylpyridine, 2,6-dimethylpyridine, 2,4-dimethylpyridine, thiophene, 2-methylthiophene, 2,3-dimethylthiophene, piperidine, phosphinine, pyrrole, 2-methylpyrrole, aniline, p-toluidine, tetrahydrofuran, 2,3-dimethyltetrahydrofuran, 2,5-tetrahydrofuran, 3,4-dihydro-2H-pyrene, furan, 2-methylfuran, 2,3-dimethylfuran, 2,5-dimethylfuran, diethyl ether, methyl t-butyl ether and triethylamine, without limitation.

In addition, the catalyst composition including the isomers and the cocatalyst may be used as a supported state on a support. As the support, silica-alumina, silica-magnesia, etc. may be used, and other optional support known in this art may be used. In addition, this support may be used as a dried state at a high temperature. The drying temperature may be, for example, from 180° C. to 800° C. In the case that the drying temperature is excessively low and less than 180° C., an excessive amount on the support may react with the promoter and deteriorate the performance. In the case that the drying temperature is excessively high and exceeds 800° C., the amount of a hydroxyl group on the surface of the support may decrease and decrease reaction site with the cocatalyst.

According to another embodiment of the present application, the compound represented by the above Formula 12 may be any alkylaluminoxane, without specific limitation. Preferably, methylaluminoxane, ethylaluminoxane, isobutylaluminoxane, butylaluminoxane, etc. may be used, and methylaluminoxane may be particularly preferably used.

According to another embodiment of the present application, the compound represented by the above Formula 13 is not specifically limited and may include trimethylaluminum, triethylaluminum, triisobutylaluminum, tripropylaluminum, tributylaluminum, dimethylchloroaluminum, triisopropylaluminum, tri-s-butylaluminum, tricyclopentylaluminum, tripentylaluminum, triisopentylaluminum, trihexylaluminum, trioctylaluminum, ethyldimethylaluminum, methyldiethylaluminum, triphenylaluminum, tri-p-tolylaluminum, dimethylaluminummethoxide, dimethylaluminumethoxide, trimethylboron, triethylboron, triisobutylboron, tripropylboron, tributylboron, etc. Particularly, the compound may preferably be selected from trimethylaluminum, triethylaluminum and triisobutylaluminum.

According to another embodiment of the present application, the compound represented by the above Formula 14 is not specifically limited and may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetraphenylaluminum, N,N-diethylaniliniumtetrapentafluorophenylaluminum, diethylammoniumtetrapentatetraphenylaluminum, triphenylphosphoniumtetraphenylaluminum, trimethylphosphoniumtetraphenylaluminum, triethylammoniumtetraphenylaluminum, tributylammoniumtetraphenylaluminum, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, triphenylcarboniumtetra(p-trifluoromethylphenyl)boron, triphenylcarboniumtetrapentafluorophenylboron, etc.

According to another embodiment of the present application, the olefin monomer may include an alpha-olefin monomer, a cyclic olefin monomer, a diene olefin monomer, a triene olefin monomer, a styrene monomer, etc., and may be obtained by homopolymerizing one kind thereof or by blending at least two thereof.

The alpha-olefin monomer includes an aliphatic olefin having 2 to 24 carbon atoms, preferably, 2 to 12 carbon atoms, and more preferably, 2 to 8 carbon atoms, and particularly includes ethylene, propylene, 1-butene, 1-pentene, 3-methyl-1-butene, 1-hexene, 4-methyl-1-pentene, 3-methyl-1-pentene, 1-heptene, 1-octene, 1-decene, 4,4-dimethyl-1-pentene, 4,4-diethyl-1-hexene, 3,4-dimethyl-1-hexene, etc. In addition, the alpha-olefin may be homopolymerized or alternating, random or block copolymerized. The copolymerization of the alpha-olefin include the copolymerization of ethylene with the alpha-olefin monomer having 2 to 12 carbon atoms, preferably having 2 to 8 carbon atoms (ethylene with propylene, ethylene with 1-butene, ethylene with 1-hexene, ethylene with 4-methyl-1-pentene and ethylene with 1-octene) and the copolymerization of propylene with the alpha-olefin monomer having 2 to 12 carbon atoms, preferably having 2 to 8 carbon atoms (propylene with 1-butene, propylene with 4-methyl-1-pentene, propylene with 4-methyl-1-butene, propylene with 1-hexene and propylene with 1-octene).

According to an embodiment of the present invention, the copolymerization may be the copolymerization of ethylene and the alpha-olefin monomer having 2 to 12 carbon atoms.

In the copolymerization of the ethylene or propylene with other alpha-olefin monomer, the amount of the other alpha-olefin may be selected from less than or equal to 90 mol % based on the total amount of the monomer. In general, the amount of the other alpha-olefin may be less than or equal to 40 mol %, preferably less than or equal to 30 mol %, and more preferably less than or equal to 20 mol % for an ethylene copolymer, and may be from 1 to 90 mol %, preferably from 5 to 90 mol %, and more preferably from 10 to 70 mol % for a propylene copolymer.

For example, when the copolymerization is the copolymerization of ethylene and the alpha-olefin monomer having 2 to 12 carbon atoms, the amounts added of the ethylene and the alpha-olefin monomer having 2 to 12 carbon atoms may be 1:0.2 to 4 by the weight ratio.

According to an embodiment of the present invention, the physical properties of the olefin-based polymer according to an embodiment of the present invention may be changed according to the amount added of the alpha-olefin monomer with respect to that of the ethylene.

For example, when the amounts added of the ethylene and the alpha-olefin monomer is 1:0.2 to 4, and preferably 1:0.2 to 3.5 by the weight ratio, the density of the olefin-based polymer prepared may be in a density range of about 0.85 to 0.91 g/cc.

In addition, according to a method of preparing an olefin-based polymer according to an embodiment, when the amounts added of the ethylene and the alpha-olefin monomer may be 1:0.4 to 2.3, and may preferably be 0.8 to 1:1.8, and the density of the olefin-based polymer prepared may be in a density range of about 0.861 to 0.885 g/cc.

Meanwhile, the cyclic olefin may include 3 to 24 carbon atoms, and may preferably include 3 to 18 carbon atoms. Particularly, cyclopentene, cyclobutene, cyclehexene, 3-methylcyclohexene, cyclooctene, tetracyclodecene, octacyclodecene, dicyclopentadiene, norbornene, 5-methyl-2-norbornene, 5-ethyl-2-norbornene, 5-isobutyl-2-norbornene, 5,6-dimethyl-2-norbornene, 5,5,6-trimethyl-2-norbornene and ethylenenorbornene may be used. The cyclic olefin may be copolymerized with the alpha-olefin, and in this case, the amount of the cyclic olefin may be from 1 to 50 mol % and may preferably be 2 to 50 mol % with respect to a copolymer.

In addition, the diene and triene may be a polyene having two or three double bonds and 4 to 26 carbon atoms. Particularly, 1,3-butadiene, 1,4-pentadiene, 1,4-hexadiene, 1,5-hexadiene, 1,9-decadiene, 2-methyl-1,3-butadidne, etc. may be used. The styrene may preferably be styrene or styrene substituted with an alkyl group having 1 to 10 carbon atoms, an alkoxy group having 1 to 10 carbon atoms, a halogen group, an amine group, a silyl group, a halogenated alkyl group, etc.

According to another embodiment of the present application, the polymerization step may be performed in a hydrocarbon solvent via liquid phase, slurry phase, bulk phase or gas phase polymerization.

The catalyst composition may have a homogeneous liquid state, a supported state on a support or an insoluble particle state of a support, and so, the polymerization may be performed via the liquid phase, the slurry phase, the bulk phase or the gas phase polymerization. In addition, polymerization conditions of each polymerization method may be diversely modified according to the state of a catalyst (homogeneous phase or inhomogeneous phase (supported type)), a polymerization method (liquid polymerization, slurry polymerization, gas polymerization), target polymerization result or a polymer type. The modification degree may be easily determined by an expert in this field.

The hydrocarbon solvent dissolved or diluted in an aliphatic hydrocarbon solvent having 5 to 12 carbon atoms such as pentane, hexane, heptane, nonane, decane and an isomer thereof, an aromatic hydrocarbon solvent such as toluene and benzene, or a hydrocarbon solvent substituted with a chlorine atom such as dichloromethane and chlorobenzene, may be used alone or as a mixture of at least two thereof and injected. At least one of the solvent dissolved or diluted may be mixed and injected. The solvent used may preferably be treated with a small amount of alkylaluminum to remove a trace amount of water or air functioning as a catalytic poison, and a cocatalyst may be further included.

The alkylaluminum may include, for example, trialkylaluminum, dialkyl aluminum halide, alkyl aluminum dihalide, aluminum dialkyl hydride or alkyl aluminum sesqui halide, etc. More particularly, $Al(C_2H_5)_3$, $Al(C_2H_5)_2H$, $Al(C_3H_7)_3$, $Al(C_3H_7)_2H$, $Al (i-C_4H_9)_2H$, $Al(C_8H_{17})_3$, $Al(C_{12}H_{25})_3$, $Al(C_2H_5) (C_{12}H_{25})_2$, $Al (i-C_4H_9) (Cl_2H_{25})_2$, $Al (i-C_4H_9)_2H$, $Al(i-C_4H_9)_3$, $(C_2H_5)_2AlCl$, $(i-C_3H_9)_2AlCl$ or $(C_2H_5)_3Al_2Cl_3$ etc. may be used. These organic aluminum compounds may be continuously inserted in each reactor and may be inserted by the molar ratio from about 0.1 to 10 mol per 1 kg of a reaction medium inserted in the reactor to remove water appropriately.

According to another embodiment of the present application, in the polymerization step of the olefin monomer using the catalyst composition, the amount of the catalyst composition including the isomer represented by the above Formula 5 or 6 is not specifically limited, however the concentration of the central metal of the catalyst composition including the isomer represented by the above Formula 5 or 6 in a reaction system used for the polymerization may preferably be $10^{-8}$ to $10^1$ mol/l, and more preferably be $10^{-7}$ to $10^{-2}$ mol/l.

According to another embodiment of the present application, the polymerization step may be performed in a batch type reactor or a continuous type reactor, and may preferably be performed in a continuous type reactor.

According to another embodiment of the present application, the polymerization step may be performed in the presence of an inert gas such as an argon gas or a nitrogen gas.

The inert gas may be, for example, a nitrogen gas or a hydrogen gas alone or a mixture thereof.

By using the inert gas, the suppression of the catalyst activity due to the injection of water or impurities in the air may be prevented. The amount ratio of the inert gas:the olefin monomer inserted may be from about 1:10 to about 1:100, without limitation. In the case that the amount of the inert gas is excessively small, the reaction of the catalyst composition may be violent, and the preparation of the olefin-based polymer having molecular weight and molecular weight distribution may become difficult. In the case that an excessive amount of the inert gas is inserted, the activity of the catalyst composition may be insufficiently attained.

According to an embodiment of the present application, an olefin-based polymer prepared by the method of preparing an olefin-based polymer is provided.

According to an embodiment of the present application, the olefin-based polymer includes a mixed olefin-based polymer of at least two polyolefin units having different crystallinity.

According to another embodiment of the present application, the olefin-based polymer is separated into a peak for a first semi-crystalline olefin-based polymer P1 and a peak for a second semi-crystalline olefin-based polymer P2 in TREF.

The peak for a first semi-crystalline olefin-based polymer has lower density and lower elution temperature Te1 than the peak for a second semi-crystalline olefin-based polymer. The peak for a second semi-crystalline olefin-based polymer has relatively higher density and higher elution temperature Te2 than the peak for a first semi-crystalline olefin-based polymer.

In the present invention, a polymer including two of Te1 and Te2 when measuring TREF and having narrow molecular weight distribution may be provided.

The olefin-based polymer according to the present invention includes a first semi-crystalline olefin-based polymer and a second semi-crystalline olefin-based polymer and has a peak for a first semi-crystalline olefin-based polymer P1 and a peak for a second semi-crystalline olefin-based polymer P2 in a temperature range from −20° C. to 130° C. when measuring TREF. Te of each peak is expressed by Te1 and Te2, respectively.

The olefin-based polymer according to an embodiment of the present invention may further include at least one peak including an amorphous peak in a minimum temperature (extremely low temperature) range from −20° C. to −10° C. other than the two semi-crystalline peaks. A common olefin-based polymer has one semi-crystalline peak; however the olefin-based polymer according to an embodiment of the present invention has two semi-crystalline peaks, thereby increasing mechanical properties, etc.

The measuring of the TREF in this application may be conducted by using, for example, a TREF apparatus of PolymerChar Co. and using an o-dichlorobenzene solvent while elevating the temperature from −20° C. to 130° C.

When measuring TREF with respect to the olefin-based polymer according to an embodiment of the present invention, the Te1 may be present at a relatively lower temperature than the Te2. When the density of the olefin-based polymer is in a range from 0.85/cc to 0.91 g/cc, Te1 may be in a range from −20° C. to 100° C., and Te2 may be in a range from 00° C. to 130° C.

The Te used in the present application means the temperature at the highest point of each peak in a TREF elution graph expressed by an elution amount with respect to temperature (dC/dT), and a fractional ratio may be calculated as an integration value of a temperature-elution amount graph.

According to an even further another embodiment of the present invention, when measuring TREF, the fractional ratio of the peak for a first semi-crystalline olefin-based polymer P1 may be from 5 to 95%, may particularly be from 10 to 90%, and may more particularly be from 20 to 90%. In addition, the fractional ratio of the peak for a second semi-crystalline olefin-based polymer P2 may be from 5 to 95%, may particularly be from 10 to 90%, and may more particularly be from 10 to 80%.

In addition, for the calculation of the fractional ratio, the initiation point of each peak in the graph of an elution amount with respect to the temperature (dC/dT) is defined as a point initiating the elution of the polymer on the basis of a base line, and the end point of each peak is defined as a point terminating the elution of the polymer on the basis of the base line.

In the case that the peak for a first semi-crystalline olefin-based polymer P1 and the peak for a second semi-crystalline olefin-based polymer P2 are partially overlapped, a point where an elution amount value (dC/dT) is the lowest in an overlapped area may be defined as the terminal point of the P1 peak and as the initiation point of the P2 peak.

In addition, a peak exhibited at a temperature range from −20° C. to −10° C. is shown by the blending of an amorphous polymer and a low crystalline polymer, and the peak exhibited at this position may be treated by adding to the fractional ratio of the P1 peak.

In addition, the olefin-based polymer according to an embodiment of the present invention includes Tm1 and Tm2, which are melting points Tms obtained in a DSC graph. In the density range of the olefin-based polymer from 0.85 to 0.91 g/cc, the Tm1 may be in a range from −30 to 120° C., and the Tm2 may be in a range from −10 to 140° C.

When a polymer is prepared using a common metallocene catalyst, one Tm is present. However, when two Tms are present, crystal may be melted and crystallized at different temperatures, and thermal stability and mechanical strength may increase.

In addition, when a blend catalyst of at least two is used, two Tms may be present. However, in this case, the activity and copolymerization degree of each in the blend catalyst are difficult to expect and control, and the preparation of an olefin-based polymer having appropriate properties according to use may become difficult. In addition, since the blending of at least two catalyst components may be inhomogeneous, the control of quality may be difficult.

The Tm used in the present application means the highest point of each peak in the temperature-heat flow graph of DSC.

Meanwhile, the olefin-based polymer according to an embodiment of the present invention has melting index (MI) when measured under the conditions of 190° C. and 2.16 kg weight according to ASTM D1238, from about 0.1 to about 2,000 g/10 min, preferably from about 0.1 to about 1,000 g/10 min, and more preferably from about 0.1 to 500 g/10 min, without limitation.

The weight average molecular weight of the olefin-based polymer may be from about 10,000 to about 500,000 g/mol and may preferably be from about 20,000 to about 200,000 g/mol, without limitation.

According to an embodiment of the present invention, the MWD of the olefin-based polymer may be from about 1.0 to about 3.0, may preferably be from about 1.5 to 3.0, and may more preferably be from 2.5 to 2.8.

According to another embodiment of the present application, the density of the olefin-based polymer is less than or equal to 0.91 g/cc, and preferably, 0.85 to 0.91 g/cc.

According to another embodiment of the present application, the olefin-based polymer may be used for hollow molding, extrusion molding or injection molding.

Hereinafter, the present invention will be explained in particular with reference to the following examples. However, the following examples are illustrated to assist the understanding of the present invention, and the scope of the present invention is not limited thereto.

MODE FOR CARRYING OUT THE INVENTION

Synthesis of Ligand and Transition Metal Compound

Organic reagents and solvents were purchased from Aldrich Co. and purified by a standard method unless otherwise specifically stated. In all synthetic steps, the contact of the air and moisture were blocked to improve the reproducibility of experiments.

Preparation Example 1

A 8-(1,2-dimethyl-1H-benzo[b]cyclopenta[d]thiophen-3-yl)-2-methyl-1,2,3,4-tetrahydroquinoline compound

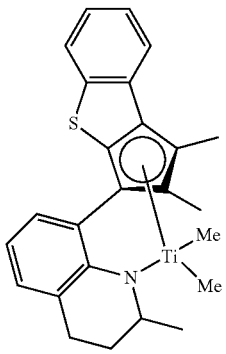

nBuLi (14.9 mmol, 1.1 eq) was slowly added drop by drop in a solution of 2-methyl-1,2,3,4-tetrahydroquinoline (2 g, 13.6 mmol) dissolved in 10 mL of ether at −40° C. The temperature was slowly elevated to room temperature, and the reaction mixture was stirred at room temperature for 4 hours. The temperature was lowered to −40° C. again and $CO_2(g)$ was inserted, and the reaction was maintained for 0.5 hours at a low temperature. The temperature was slowly elevated, and remaining $CO_2(g)$ was removed via a bubbler. THF (17.6 mmol, 1.4 ml) and tBuLi (10.4 mmol, 1.3 eq) were inserted in the reaction mixture at −20° C., following by aging at a low temperature at −20° C. for 2 hours. The ketone (1.9 g, 8.8 mmol) was dissolved in diethyl ether and slowly added drop by drop in the reaction mixture. After stirring at room temperature for 12 hours, 10 mL of water was inserted and hydrochloric acid (2N, 60 mL) was added in the reactant, followed by stirring for 2 minutes. Organic solvents were extracted and the reactant was neutralized with a $NaHCO_3$ aqueous solution. Then, the organic solvent was extracted and dried with $MgSO_4$. Through silica gel column chromatography, a yellow oil (1.83 g, 60% yield) was obtained.

1H NMR (C6D6): δ 1.30 (s, 3H, CH3), 1.35 (s, 3H, CH3), 1.89-1.63 (m, 3H, Cp-H quinoline-CH2), 2.62-2.60 (m, 2H, quinoline-CH2), 2.61-2.59 (m, 2H, quinoline-NCH2), 2.70-2.57 (d, 2H, quinoline-NCH2), 3.15-3.07 (d, 2H, quinoline-NCH2), 3.92 (broad, 1H, N—H), 6.79-6.76 (t, 1H, aromatic), 7.00-6.99 (m, 2H, aromatic), 7.30-7.23 (m, 2H, aromatic), 7.54-7.53 (m, 1H, aromatic), 7.62-7.60 (m, 1H, aromatic) ppm A 8-(1,2-dimethyl-1H-benzo[b]cyclopenta[d]thiophen-3-yl)-2-methyl-1,2,3,4-tetrahydroquinoline-titanium dichloride compound nBuLi (3.0 mmol, 2.1 eq) was slowly added drop by drop in the ligand (1.0 g, 2.89 mmol) at −20° C. The formation of a yellow slurry was observed, and the temperature was slowly elevated to room temperature, followed by stirring at room temperature for 12 hours. TiCl4DME (806 mg, 2.89 mmol, 1.0 eq) was added drop by drop, followed by stirring at room temperature for 12 hours. After removing solvents, the reactant was extracted with toluene to obtain a red solid (700 mg, 52% yield).

1H NMR (C6D6): δ 1.46-1.467 (t, 2H, quinoline-NCH2), 1.85 (s, 3H, Cp-CH3), 1.79 (s, 3H, Cp-CH3), 2.39 (s, 3H, Cp-CH3), 2.37 (s, 3H, Cp-CH3), 2.10-2.07 (t, 2H, quinoline-NCH2), 5.22-5.20 (m, 1H, N—CH), 5.26-5.24 (m, 1H, N—CH), 6.89-6.87 (m, 2H, aromatic) 6.99-6.95 (m, 1H, aromatic), 7.19-7.08 (m, 2H, aromatic), 7.73-7.68 (m, 1H, aromatic) ppm

Preparation of Olefin-Based Polymer

Preparation of Ethylene-Alpha-Olefin Copolymer

Example 1

In a 1.5 L autoclave continuous process reactor, a hexane solvent and 1-octene were added, and the temperature of the upper end portion of the reactor was pre-heated to 160° C. A triisobutylaluminum compound, the metallocene compound thus obtained and dimethylanilinium tetrakis(pentafluorophenyl)borate cocatalyst were added in the reactor at the same time. Then, ethylene was inserted in the autoclave reactor, and the reaction mixture was maintained under the pressure of 89 bar at 160° C. for 30 minutes, and a copolymerization reaction was performed in a continuous process to produce a copolymer. After that, a remaining ethylene gas was exhausted out, and a polymer solution was dried in a vacuum oven and dried for at least 12 hours. Then, physical properties thereof were measured.

Example 2

An olefin-based polymer was prepared by the same procedure described in the above Example 1 except for adding materials in conditions shown in the following Table 1.

Example 3

An olefin-based polymer was prepared by the same procedure described in the above Example 1 except for using 1-butene instead of 1-octene as the alpha-olefin and adding materials in conditions shown in the following Table 1.

Example 4

An olefin-based polymer was prepared by the same procedure described in the above Example 1 except for using 1-butene instead of 1-octene as the alpha-olefin and adding materials in conditions shown in the following Table 1.

Example 5

An olefin-based polymer was prepared by the same procedure described in the above Example 1 except for adding materials in conditions shown in the following Table 1.

Example 6

An olefin-based polymer was prepared by the same procedure described in the above Example 1 except for adding materials in conditions shown in the following Table 1.

Example 7

An olefin-based polymer was prepared by the same procedure described in the above Example 1 except for using 1-butene instead of 1-octene as the alpha-olefin and adding materials in conditions shown in the following Table 1.

Example 8

An olefin-based polymer was prepared by the same procedure described in the above Example 1 except for using 1-butene instead of 1-octene as the alpha-olefin and adding materials in conditions shown in the following Table 1.

Comparative Example 1

An olefin-based polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl($\eta^5$-tetramethylCp) (t-butylamido)] $TiCl_2$ compound) in conditions shown in the following Table 1.

Comparative Example 2

An olefin-based polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl($\eta^5$-tetramethylCp) (t-butylamido)] $TiCl_2$ compound) in conditions shown in the following Table 1.

Comparative Example 3

An olefin-based polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl($\eta^5$-tetramethylCp) (t-butylamido)]$TiCl_2$ compound) in conditions shown in the following Table 1.

Comparative Example 4

An olefin-based polymer was prepared by the same procedure described in the above Example 1 except for using a mixture of a first metallocene compound ([(1,2,3,4-tetrahydroquinolin-8-yl)tetramethylcyclopentadienyl-eta5,kappa-N]titanium dimethyl) and a second metallocene compound ([methyl(6-t-butoxyhexyl)silyl($\eta^5$-tetramethylCp) (t-butylamido)] $TiCl_2$ compound) in conditions shown in the following Table 1.

Comparative Example 5

An ethylene-1-octene copolymer of LG Chem. Ltd. (trade name; LC670, density=0.870 g/cc, MI2.16=5.0) prepared by using only one kind of a metallocene catalyst was prepared.

Comparative Example 6

An ethylene-1-octene copolymer of LG Chem. Ltd. (trade name; LC760, density=0.863 g/cc, MI2.16=13.0) prepared by using only one kind of a metallocene catalyst was prepared.

Comparative Example 7

An ethylene-1-octene copolymer of Dow Co. (trade name; HM7387, density=0.872 g/cc, MI2.16<5.0) was prepared.

Experimental Example 1

Measuring TREF

TREF was measured by using a TREF machine of PolymerChar and an o-dichlorobenzene solvent in a range of −20 to 130° C.

80 mg of a polymer sample was dissolved in 20 ml of an o-dichlorobenzene solvent at 135° C. for 30 minutes and stabilized at 95° C. for 30 minutes. The solution thus obtained was introduced in a TREF column, cooled to −20° C. by the temperature decreasing rate of 0.5° C./min, and supported for 2 minutes. Then, the temperature was increased from −20° C. to 130° C. by the temperature increasing rate of 1° C./min, and the concentration of an eluted polymer was measured while flowing the o-dichlorobenzene solvent in the column by the flowing rate of 0.5 mL/min.

Experimental Example 2

Measuring Other Physical Properties

The amounts of a cis isomer and a trans isomer of a catalyst composition were measured by using $^1$H-NMR.

The density of a polymer: measured by ASTM D-792.

MWD; obtained by measuring number average molecular weight (Mn) and weight average molecular weight (Mw) using gel permeation chromatography (GPC), and dividing the weight average molecular weight by the number average molecular weight.

MI of a polymer was measured by ASTM D-1238 (Condition E, 190° C., 2.16 kg weight).

Experimental Example 3

Measuring DSC

DSC was obtained by using Differential Scanning Calorimeter 6000 manufactured by PerKinElmer Co. That is, the temperature was elevated to 200° C., this temperature was maintained for 1 minute, the temperature was decreased to −100° C., and the temperature was elevated again. The apex of a DSC curve was set to melting point. In this case, the temperature increasing and decreasing rates were 10° C./min, and the melting point was obtained during the second elevation of the temperature. The DSC analysis results of the polymer according to the present invention are illustrated in the following Table 2.

TABLE 1

| Sample | Hexane kg/h | Ethylene kg/h | 1-Octene kg/h | 1-Butene kg/h | Cat. μmol/min | Co-cat. Unit μmol/min | Scavenger μmol/ | P minbar | Temp. °C. | Density g/cc | MI2.16 g/10 min |
|---|---|---|---|---|---|---|---|---|---|---|---|
| Example 1 | 5.02 | 0.87 | 0.92 | — | 0.63 | 1.89 | 0.03 | 89 | 159.0 | 0.870 | 3.2 |
| Example 2 | 4.79 | 0.87 | 1.20 | — | 0.60 | 1.80 | 0.03 | 89 | 159.8 | 0.861 | 10.8 |
| Example 3 | 5.10 | 0.87 | — | 0.95 | 0.35 | 1.05 | 0.04 | 89 | 161.1 | 0.871 | 0.24 |
| Example 4 | 5.10 | 0.87 | — | 0.9 | 0.35 | 1.05 | 0.04 | 89 | 161.1 | 0.873 | 0.23 |
| Example 5 | 5.33 | 0.87 | 0.77 | — | 0.50 | 1.50 | 0.03 | 89 | 159.8 | 0.885 | 0.90 |
| Example 6 | 4.96 | 0.87 | 1.05 | — | 0.63 | 1.89 | 0.03 | 89 | 160.0 | 0.867 | 6.0 |
| Example 7 | 5.34 | 0.87 | — | 1.10 | 0.50 | 1.50 | 0.03 | 89 | 160.7 | 0.865 | 9.33 |
| Example 8 | 4.65 | 0.87 | — | 1.50 | 0.50 | 1.50 | 0.03 | 89 | 160.5 | 0.862 | 32.70 |
| Com. Example 1 | 5.61 | 0.87 | 1.00 | — | 0.35 | 1.05 | 0.03 | 89 | 160.2 | 0.872 | 5.1 |
| Com. Example 2 | 5.10 | 0.87 | 1.25 | — | 0.43 | 1.29 | 0.03 | 89 | 159.4 | 0.863 | 11.1 |
| Com. Example 3 | 5.10 | 0.87 | — | 0.97 | 0.20 | 0.60 | 0.03 | 89 | 161.0 | 0.870 | 0.38 |
| Com. Example 4 | 5.10 | 0.87 | — | 0.92 | 0.14 | 0.42 | 0.03 | 89 | 160.0 | 0.873 | 0.28 |
| Com. Example 5 | | | | | | | | | | 0.869 | 5.1 |
| Com. Example 6 | | | | | | | | | | 0.862 | 11.0 |
| Com. Example 7 | | | | | | | | | | 0.872 | 0.27 |

As shown in the above Table 1, when compared to Comparative Examples 1 and 2, Examples 1 and 2 exhibited similar degree of density and molecular weight with relatively small amount of octene, and better copolymerization properties.

In addition, with respect to Example 1 and Comparative Example 1, having similar density range of about 0.870 to about 0.872 g/cc, the amount of the octene used in Example 1 decreased by about 8% when compared to that used in Comparative Example 1.

In addition, with respect to Example 2 and Comparative Example 2, having similar density range of about 0.860 to about 0.863 g/cc, the amount of the octene used in Example 2 decreased by about 4% when compared to that used in Comparative Example 2.

Meanwhile, the change of the physical properties of Examples 1 to 8 according to the present invention was found according to the amount added of 1-butene or 1-octene, which are alpha-olefin monomers with respect to ethylene.

Particularly, in the case that the amount added of ethylene and 1-butene by weight is from about 1:1 to about 1:1.8, the olefin-based polymer has a density range of about 0.862 to about 0.873 g/cc.

In addition, in the case that the amount added of ethylene and 1-octene by weight is about 0.8 to 1:1.4, the olefin-based polymer has a density range of about 0.861 to about 0.885 g/cc.

Thus, it would be found that the density of the olefin-based polymer may be controlled by the amount added of the ethylene and the alpha-olefin monomer.

TABLE 2

| Sample | Density g/cc | MI2.16 g/10 min | Tm1 °C. | Tm2 °C. | Mw Unit | MWD | Te1 °C. | Te2 °C. | P1 % | P2 % |
|---|---|---|---|---|---|---|---|---|---|---|
| Example 1 | 0.870 | 3.2 | 46.3 | 85.2 | 117975 | 2.36 | 16.6 | 57.4 | 75.9 | 24.1 |
| Example 2 | 0.861 | 10.8 | 20.0 | 75.2 | 98328 | 2.21 | 2.8 | 47.4 | 74.0 | 26.0 |
| Example 3 | 0.871 | 0.24 | 29.7 | 81.0 | 169671 | 2.31 | 11.0 | 57.4 | 67.2 | 32.7 |
| Example 4 | 0.873 | 0.23 | 34.0 | 82.4 | 162989 | 2.26 | 13.4 | 58.2 | 70.3 | 29.7 |
| Com. Example 1 | 0.872 | 5.1 | 56.1 | 100.6 | 98993 | 2.51 | 23.6 | 74.0 | 91.7 | 8.3 |
| Com. Example 2 | 0.863 | 11.1 | 40.8 | 96.1 | 84514 | 2.52 | 7.0 | 68.6 | 91.8 | 8.2 |
| Com. Example 3 | 0.870 | 0.38 | 52.3 | 99.5 | 129631 | 2.34 | 28.0 | 71.4 | 93.5 | 6.5 |
| Com. Example 4 | 0.873 | 0.28 | 46.7 | 96.4 | 128500 | 2.36 | 24.6 | 72.0 | 87.6 | 12.4 |
| Com. Example 5 | 0.869 | 5.1 | 56.9 | — | 107847 | 2.44 | 23.6 | — | 100.0 | — |
| Com. Example 6 | 0.862 | 11.0 | 48.9 | — | 96230 | 2.41 | 15.6 | — | 100.0 | — |
| Com. Example 7 | 0.872 | 0.27 | 49.1 | — | 163099 | 2.31 | 30.4 | — | 100.0 | — |

As shown in the above Table 2, different from Comparative Examples 5 to 7, the olefin-based polymers prepared by using a single catalyst in Examples 1 to 4 according to the present invention exhibited two semi-crystalline olefin-based polymer peaks P1 and P2 when measuring TREF in a density range of 0.86 to 0.873 g/cc, and so had two Te1 and Te2.

Meanwhile, even though different from the catalyst of the present invention, the olefin-based polymers prepared by using a single catalyst in Comparative Examples 5 to 7 also exhibited one peak of P1 when measuring TREF in a density range of 0.86 to 0.873 g/cc, and so had only one T1.

In addition, the olefin-based polymers of Examples 1 to 4 according to the present invention exhibited two Tms different from the olefin-based polymers of Comparative Examples 5 to 7 in the results of DSC analysis. The olefin-based polymers of the examples according to the present invention used a single catalyst and had two Tms without exhibiting significant increase of MWD when compared to those of Comparative Examples 1 to 4 using two kinds of metallocene catalysts.

The copolymer of a double formation olefin-based polymer as in the examples of the present invention has merits of exhibiting high service temperature without loosing elastomer properties at a high temperature due to a composition having a high melting point.

Meanwhile, when comparing the changing ratio of the fractional ratio of P1 and P2 of Examples 3 and 4 and Comparative Examples 3 and 4, having similar degree of density and melting index, the changing ratio of the fractional ratio of P1 and P2 were less than or equal to about 10% for Examples 3 and 4, and the changing ratio of the fractional ratio of P1 and P2 were greater than or equal to about 50% for Comparative Examples 3 and 4.

Thus, according to the method of preparing an olefin-based polymer according to the examples of the present invention, the control of the fractional ratio of TREF peaks is good, and a more stable olefin-based polymer may be prepared.

While this invention has been particularly shown and described with reference to preferred embodiments thereof and drawings, it will be understood by those skilled in the art that various changes in form and details may be made therein without departing from the spirit and scope of the invention as defined by the appended claims.

The invention claimed is:

1. A method of preparing an olefin-based polymer, comprising polymerizing an olefin monomer in the presence of a catalyst composition including a transition metal compound of the following Formula 1:

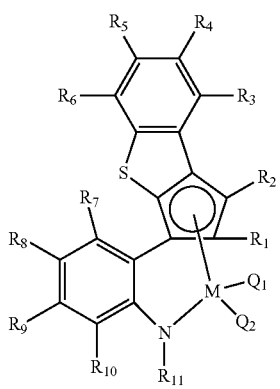

<Formula 1> in the above Formula 1,

M is a transition metal in group 4, $Q_1$ and $Q_2$ are the same or different and independently hydrogen; halogen; alkyl having 1 to 20 carbon atoms; alkenyl having 2 to 20 carbon atoms; aryl having 6 to 20 carbon atoms; alkylaryl having 6 to 20 carbon atoms; arylalkyl having 7 to 20 carbon atoms; alkyl amido having 1 to 20 carbon atoms; aryl amido having 6 to 20 carbon atoms; or alkylidene having 1 to 20 carbon atoms, $R_1$ to $R_6$ are the same or different and independently hydrogen; silyl; alkyl having 1 to 20 carbon atoms; alkenyl having 2 to 20 carbon atoms; aryl having 6 to 20 carbon atoms; alkylaryl having 7 to 20 carbon atoms; arylalkyl having 7 to 20 carbon atoms; or a metalloid radical of a metal in group 14 substituted with hydrocarbyl having 1 to 20 carbon atoms; $R_1$ and $R_2$ optionally connected from each other, or at least two of $R_3$ to $R_6$ optionally connected to each other to form an aliphatic ring having 5 to 20 carbon atoms or an aromatic ring having 6 to 20 carbon atoms; the aliphatic ring or the aromatic ring optionally substituted with halogen, alkyl having 1 to 20 carbon atoms, alkenyl having 2 to 20 carbon atoms or aryl having 6 to 20 carbon atoms, and $R_7$ to $R_{11}$ are the same or different and independently hydrogen; alkyl having 1 to 20 carbon atoms; alkenyl having 2 to 20 carbon atoms; aryl having 6 to 20 carbon atoms; alkylaryl having 7 to 20 carbon atoms; or arylalkyl having 7 to 20 carbon atoms; at least two adjacent to each other of $R_7$ to $R_{11}$ optionally connected to each other to form an aliphatic ring having 5 to 20 carbon atoms or an aromatic ring having 6 to 20 carbon atoms; the aliphatic ring or the aromatic ring optionally substituted with halogen, alkyl having 1 to 20 carbon atoms, alkenyl having 2 to 20 carbon atoms or aryl having 6 to 20 carbon atoms.

2. The method of claim 1, wherein the olefin-based polymer comprises a first semi-crystalline olefin-based polymer and a second semi-crystalline olefin-based polymer.

3. The method of claim 2, wherein a fractional ratio of a peak for a first semi-crystalline olefin-based polymer (P1) is 5 to 95%, and a fractional ratio a peak for a second semi-crystalline olefin-based polymer (P2) is 5 to 95% when measuring temperature rising elution fractionation (TREF) of the olefin-based polymer.

4. The method of claim 1, wherein $R_1$ and $R_2$ are alkyl having 1 to 20 carbon atoms.

5. The method of claim 1, wherein M is Ti, Hf or Zr.

6. The method of claim 1, wherein the catalyst composition further comprises at least one kind of a cocatalyst.

7. The method of claim 6, wherein the cocatalyst comprises at least one selected from the following Formulae 12 to 14:

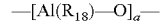                                                     <Formula 12> in the above Formula, $R_{18}$ is independently a halogen radical; a hydrocarbyl radical having 1 to 20 carbon atoms; or a hydrocarbyl radical having 1 to 20 carbon atoms substituted with halogen, and a is an integer greater than or equal to 2,

                                                     <Formula 13> in the above Formula, D is aluminum or boron, and $R_{18}$ is the same as in the above Formula 12,

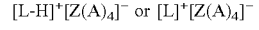                                                     <Formula 14> in the above Formula, L is a neutral or cationic Lewis acid, H is a hydrogen atom, Z is an element in group 13, and A is independently aryl having 6 to 20 carbon atoms or alkyl having 1 to 20 carbon atoms, where at least one hydrogen atom optionally substituted with a substituent, and the substituent is halogen, hydrocarbyl having 1 to 20 carbon atoms, alkoxy having 1 to 20 carbon atoms, or aryloxy having 6 to 20 carbon atoms.

8. The method of claim 1, wherein the polymerizing of the olefin monomer comprises homopolymerizing of at least one monomer of an alpha-olefin monomer, a cyclic olefin monomer, a diene olefin monomer, a triene olefin monomer or a styrene monomer, or copolymerizing at least two monomers.

9. The method of claim 8, wherein the copolymerizing is copolymerizing of ethylene and an alpha-olefin monomer having 2 to 12 carbon atoms.

10. The method of claim 9, wherein an addition amount ratio of the ethylene and the alpha-olefin monomer having 2 to 12 carbon atoms is 1:0.2 to 4 by weight.

11. The method of claim 10, wherein the density of the olefin-based polymer is in a range of 0.85 to 0.91 g/cc.

12. The method of claim 1, wherein the polymerizing is performed by a liquid phase, a slurry phase, a bulk phase or a gaseous phase polymerization in a hydrocarbon solvent.

13. The method of claim 1, wherein the polymerizing is performed in a continuous type reactor.

14. The method of claim 1, wherein the polymerizing is performed in the presence of an inert gas.

* * * * *